United States Patent [19]

Lim

[11] 4,407,957
[45] Oct. 4, 1983

[54] REVERSIBLE MICROENCAPSULATION OF A CORE MATERIAL

[75] Inventor: Franklin Lim, Richmond, Va.

[73] Assignee: Damon Corporation, Needham Heights, Mass.

[21] Appl. No.: 372,836

[22] Filed: Apr. 28, 1982

Related U.S. Application Data

[63] Continuation-in-part of Ser. No. 243,584, Mar. 13, 1981, abandoned, which is a continuation-in-part of Ser. No. 24,600, Mar. 28, 1979, Pat. No. 4,352,883, which is a continuation-in-part of Ser. No. 953,413, Oct. 23, 1978, abandoned.

[51] Int. Cl.$^3$ .................. C12N 11/10; C12N 11/08; C12N 11/04; C12N 5/02
[52] U.S. Cl. .................. 435/178; 435/180; 435/182; 435/241; 264/4.33; 264/4.3; 427/213.33; 427/213.31
[58] Field of Search .............. 435/174, 175, 177, 178, 435/180, 182, 241; 424/31, 34, 35, 36, 94, DIG. 7; 252/316; 264/4

[56] References Cited

U.S. PATENT DOCUMENTS

| | | | |
|---|---|---|---|
| 3,522,346 | 7/1970 | Chang | 435/188 X |
| 3,725,113 | 4/1973 | Chang | 424/101 X |
| 3,730,841 | 5/1973 | Salvatore et al. | 435/182 |
| 3,733,205 | 5/1973 | Shovers et al. | 435/262 X |
| 3,827,565 | 8/1974 | Matsumura | 435/182 X |
| 3,860,490 | 1/1975 | Guttag | 435/182 |
| 4,251,387 | 2/1981 | Lim et al. | 424/DIG. 7 |
| 4,257,884 | 3/1981 | Lim | 435/182 |

FOREIGN PATENT DOCUMENTS

| | | |
|---|---|---|
| 1600988 | 9/1970 | France . |
| 2046209 | 11/1980 | United Kingdom . |

OTHER PUBLICATIONS

Tze et al., Implantable Artificial Endocrine Pancreas Unit used to Restore Normoglycemia in Diabetic Rat., Nature, vol. 264, 1976, pp. 466–467.

Chang, T. M. S., Biomedical Applications of Immobilized Enzymes and Proteins, vol. I, Plenum Press, NY, 1977, pp. 64–90 and 142–153.

*Primary Examiner*—David M. Naff
*Attorney, Agent, or Firm*—Lahive & Cockfield

[57] ABSTRACT

Disclosed is a process for microencapsulating a core material and subsequently releasing the core material by selectively disrupting the membranes of the microcapsules. The encapsulation technique involves the formation of a semipermeable membrane, e.g., around a droplet, through the formation of multiple ionic salt bonds between a polyionic polymer in the droplet and a crosslinking polyionic polymer which possesses multiple ionic groups of opposite charge. The membrane can be selectively disrupted by exposing it first to a solution of competing crosslinking multivalent (preferably di or trivalent) ions followed by a solution of a competing polyionic polymer of the same charge as the polymer in the original droplet. Alternatively, a mixed solution of the two competing solutions may be used together. For example, a membrane comprising anionic alginate salt bonded to cationic polymer can be selectively disrupted by exposing the membrane to a mixed solution of monatomic, multivalent cations, e.g. Ca++ ions, and a water-soluble polymer have plural anionic moieties, e.g., heparin, and subsequently sequestering the monatomic cations. The process may be used to encapsulate and subsequently release cell cultures without damage to the cells.

18 Claims, No Drawings

REVERSIBLE MICROENCAPSULATION OF A CORE MATERIAL

REFERENCE TO RELATED APPLICATIONS

This application is a continuation-in-part of copending U.S. application Ser. No. 243,584, filed Mar. 13, 1981 (now abandoned) which was a continuation-in-part of U.S. Ser. No. 24,600, filed Mar. 28, 1979, now U.S. Pat. No. 4,352,883, which is a continuation-in-part of U.S. application Ser. No. 953,413, filed Oct. 23, 1978 (now abandoned). Related U.S. application Ser. Nos. 243,583 and 243,586 were filed on Mar. 13, 1981 and both are now abandoned. The disclosures of all of the foregoing applications are incorporated herein by reference.

BACKGROUND

This invention relates to a method of encapsulation which is reversible, that is, a method which may be used to encapsulate a liquid or a solid material and thereafter to release the material by selectively disrupting the capsule membranes. An important embodiment of the invention involves the microencapsulation of living cells which may subsequently be released from within the produced capsule membranes without damage.

U.S. Pat. No. 4,352,883 entitled "Encapsulation of Viable Tissue and Tissue Implantation Method," filed Mar. 28, 1979 by F. Lim discloses a microencapsulation technique which can be used to encapsulate essentially any solid or liquid material within semipermeable or substantially impermeable capsule membranes. An outstanding advantage of the process is that the conditions under which the capsule membranes are formed involve no toxic or denaturing reagents, extremes of temperature, or other conditions which damage living cells. The process of that application is accordingly well-suited for the production of microencapsulated living materials which remain viable and in a healthy state. Because the process allows a degree of control of the permeability of the membrane, it is now possible to microencapsulate cell cultures of procaryotic, eukaryotic, or other origin such that cells of the culture are protected from contaminating bacteria, high molecular weight immunoglobulins, and other potentially deleterious factors, and remain confined within a microenvironment well-suited for their continuing viability and ongoing metabolic functions. If the microcapsules are suspended in a conventional culture medium sufficient to support growth of the living cells involved, the microencapsulated cells are free to ingest substances needed for metabolism which diffuse through the membrane and to excrete their metabolic products through the capsule membrane into the surrounding medium.

SUMMARY OF THE INVENTION

The instant invention is directed to a method of selectively disrupting certain membranes synthesized during the microencapsulation procedure set forth in the above-referenced application without any detectable damage to the encapsulated core material. More specifically, the process of this invention is practiced on membranes comprising a water-insoluble matrix formed from at least two water-soluble components: a polymer which includes multiple cationic moieties (polycationic polymer, e.g. polyethylene amine); and a polymer having multiple anionic moieties (polyanionic polymer, e.g. sodium alginate gum). The two components are connected by salt-bridges between the anionic and cationic moieties to form the matrix.

The process of the invention comprises the steps of exposing membranes of the type set forth above to a solution of cations, preferably, monatomic or very low molecular weight multivalent cations, and a solution of a stripping polymer having plural anionic moieties. Preferably, these solutions are mixed together. The anionic charge of the polymer should be sufficient to disrupt the salt bridges and should preferably be equal to or greater than the charge density of the polyanionic polymer of the membrane. The solution is contacted with the capsules to allow the cations, e.g., calcium or aluminum, to compete against the polycationic polymer in the capsule membrane for anionic sites on the polyanionic polymer. Simultaneously, the stripping polymer having plural anionic moieties competes with the polyanionic polymer for cationic sites on the polymer chains. This results in "softening" or "unzipping" of the capsule membranes. To complete the disruption, the capsules are washed and then exposed to a sequestering agent to remove cations associated with the polyanionic polymer. The preferred sequestering agents are chelating agents such as citrate ions or EDTA ions. If, as in an important embodiment, the capsules contain viable cells, it is preferred to mix the sequestering agent with an isotonic saline solution.

The currently preferred cation is calcium. Examples of the stripping polymer having plural anionic groups used in the mixed solution include polysulfonic acids or (preferably) their salts, either natural or synthetic. Outstanding results have been obtained using heparin, a natural polymer containing plural sulfonate groups. Polymers containing polyphosphoric or polyacrylic acid salt moieties may also be used. The currently preferred sequestering agent is sodium citrate.

The invention also contemplates a method of encapsulating viable cells within a protective environment and subsequently releasing the cells. Thus, the invention provides what may be described as a package which maintains living cell cultures of whatever origin in a sterile, stabilizing environment in which they can undergo normal metabolism and even mitosis and from which they subsequently can be released.

Accordingly, an object of the invention is to provide a method for encapsulating living cells within permeable membranes and subsequently selectively disrupting the membranes to release the cells. Another object is to provide a process for selectively disrupting membranes. Another object is to disrupt membranes without damage to proximate living tissue. Still another object is to provide a method of encapsulating and subsequently releasing finely divided materials, liquids, and solutions.

These and other objects and features of the invention will be apparent from the following description of some important embodiments.

DESCRIPTION

The selective membrane disruption process of the invention is practiced on membranes consisting of a salt bridge-bonded matrix of a polycationic polymer and a polyanionic polymer. Usually, the membranes will have a spheroidal form defining an enclosed interior containing an encapsulated substance. However, the process may also be practiced on membranes of this type which take other than spheroidal form.

Although essentially any material (compatible with aqueous environments) in liquid or solid form can be encapsulated and subsequently released without damage by the process of this invention, its most notable utility, as presently contemplated, lies in its ability to encapsulate and subsequently release living systems such as cell cultures. Accordingly, the description which follows will be primarily confined to a discussion of the encapsulation and release of cells. Those skilled in the art will be able to adapt the process without difficulty to the encapsulation of less fragile materials.

ENCAPSULATION

The tissue or cells to be encapsulated are suspended in an aqueous medium suitable for maintenance and for supporting the ongoing metabolic processes of the particular cell type involved. Media suitable for this purpose are well known to those skilled in the art and often are available commercially. The average diameter of the cell mass or other material to be encapsulated can vary widely between a few microns to a millimeter or more. Mammalian Islets of Langerhans, for examples, are typically 50 to 200 microns in diameter. Tissue fragments and individual cells such as fibroblasts, leukocytes, lymphoblastoids, pancreatic beta, alpha or delta cells, islet of Langerhans, hepatocytes, or the cells of other tissue may be encapsulated as desired. Also, microorganisms may be encapsulated including those which have been genetically modified by recombinant DNA or other techniques.

The ongoing viability of such living matter is dependent, inter alia, on the availability of required nutrients, oxygen transfer, absence of toxic substances in the medium, and the pH of the medium. Heretofore, it has not been possible to maintain such living matter in a physiologically compatible environment while simultaneously encapsulating. The problem has been that the conditions required for membrane formation have been lethal or harmful to the tissue, and prior to the invention of the above-referenced application, no method of membrane formation which allowed tissue to survive in a healthy state had been forthcoming.

However, it has been discovered that certain water-soluble substances which are physiologically compatible with living tissue and can be rendered water-insoluble to form a shape-retaining, coherent mass, can be used to form a "temporary capsule" or protective barrier layer about individual cells, groups of cells, or tissues. Such a substance is added, typically at a concentration on the order of 1–2 weight percent, to the tissue culture medium. The solution is then formed into droplets containing tissue together with its maintenance or growth medium and is immediately rendered water-insoluble and gelled, at least in a surface layer. Thereafter, the shape-retaining temporary capsules are provided with a more permanent membrane which, in accordance with this invention, may be subsequently selectively disrupted to release the encapsulated tissue without damage. Where the material used to form the temporary capsules permits, the capsule interior may be reliquified after formation of the permanent membrane. This is done by re-establishing the conditions in the medium at which the material is soluble.

The material used to form the temporary capsules may be any non-toxic, water-soluble material which, by a change in the surrounding ionic environment or concentration, can be converted to a shape-retaining mass. The material also comprises plural, easily ionized anionic moieties, e.g., carboxyl groups, which can react by salt-bond formation with polymers containing plural cationic groups. As will be explained below, this type of material enables the deposition of the permanent membrane of a selected permeability (including substantially non-porous to a level of several hundred thousand daltons).

The presently preferred polyanionic material for forming the temporary capsule are acidic, water-soluble, natural or synthetic polysaccharide gums. Many such materials are commercially available. They are typically extracted from vegetable matter and are often used as additives to various foods. Sodium alginate is the presently preferred anionic polymer. Alginate in the molecular weight range of 150,000+ daltons may be used, but because of its molecular dimensions will usually be unable to permeate the finally formed capsule membranes. To make capsules without trapped liquid alginate, lower molecular weight alginate, e.g., 40,000–80,000 daltons can be used. In the finished capsule, the alginate can then be more easily removed from the intracapsular volume by diffusion through a membrane of sufficient porosity. Other useable polyanionic gums include acidic fractions of guar gum, carageenan, pectin, tragacanth gum, or xanthan gum.

These materials comprise glycoside-linked saccharide chains. Their free acid groups are often present in the alkali metal ion form, e.g., sodium form. If a multivalent ion such as calcium, strontium, or aluminum is exchanged for the alkali metal ion, the liquid, water-soluble polysaccharide molecules are "cross-linked" to form a water-insoluble, shape-retaining gel which can be resolubilized on removal of the ions by ion exchange or via a suquestering agent. While essentially any multivalent ion which can form a salt with the acidic gum is operable, it is preferred that physiologically compatible ions, e.g., calcium, be employed. This tends to preserve the tissue in the living state. Other multivalent cations can be used for less fragile material. Magnesium ions are ineffective in gelling sodium alginate.

A typical solution composition comprises equal volumes of a cell suspension in its medium and a one to two percent solution of gum in physiological saline. When employing sodium alginate, a 0.6 to 1.6 percent solution has been used with success.

In the next step of the encapsulation process, the gum solution containing the tissue is formed into droplets of a desired size sufficient to envelop the cells to be encapsulated. Thereafter, the droplets are immediately gelled to form shape-retaining spherical or spheroidal masses. The drop formation may be conducted by known techniques.

A tube containing an aqueous solution of multivalent cations, e.g., 1.5% $CaCl_2$ solution, is fitted with a stopper which holds a drop forming apparatus. The apparatus comprises a housing having an upper air intake nozzle and an elongate hollow body friction fitted into the stopper. A 10 cc syringe equipped with a stepping pump is mounted atop the housing with, e.g., a 0.01 inch I.D. Teflon coated needle passing through the length of the housing. The interior of the housing is designed such that the tip of the needle is subjected to a constant laminar air flow which acts as an air knife. In use, with the syringe full of solution containing the material to be encapsulated, the stepping pump is actuated to incrementally force droplets of solution from the tip of the needle. Each drop is "cut off" by the air stream and falls approximately 2.5 cm into the $CaCl_2$ solution where it is immediately gelled by absorption of calcium ions. The distance between the tip of the needle and the surface of the CaCl$_2$ solution is great enough, in this instance, to allow the sodium alginate/cell suspension to assume the most physically favorable shape; a sphere (maximum volume for minimum surface area). Air within the tube bleeds through an opening in the stopper. This results in "cross-linking" of the gel and in the formation of a high viscosity, shape-retaining protective temporary capsule containing the suspended tissue and its medium. The capsules collect in the solution as a separate phase and are separated by aspiration.

In the next step of the process, a membrane is deposited about the surface of the temporary capsules by cross-linking surface layers. This is done by subjecting the temporary capsules comprising polyanion to an aqueous solution of a polymer containing cationic groups reactive with anionic functionalities in the polyanionic polymer. Polymers containing reactive cationic groups such as free amine groups or combinations of amine and imine groups are preferred. In this situation, the polysaccharide gum is crosslinked by interaction (salt bond formation) between the carboxyl groups and the amine or imine groups of the polycationic polymer. Advantageously, permeability can be controlled within limits by selecting the molecular weight of the cross-linking polymer used and by varying exposure time and the concentration of polymer in solution. A solution of polymer having a low molecular weight, in a given time period, will penetrate further into the temporary capsules than will a high molecular weight polymer. The degree of penetration of the cross-linker has been correlated with the resulting permeability. In general, the higher the molecular weight and the less penetration, the larger the pore size. Longer exposures and more concentrated polymer solutions tend to decrease the resulting membrane's upper limit of permeability. However, the average molecular weight of the polymer is the dominant determinant. Broadly, polymers within the molecular weight range of 10,000 to 100,000 daltons or greater may be used, depending on the duration of the reaction, the concentration of the polymer solution, and the degree of permeability desired. One successful set of reaction conditions, using polylysine of average molecular weight of about 35,000 daltons, involved reaction for three minutes, with stirring, of a physiological saline solution containing 0.0167 percent polylysine. This results in membranes having an upper limit of permeability of about 100,000 daltons. Generally, higher molecular weight materials form membrane which are more difficult to subsequently disrupt as compared with lower molecular weight materials. The charge density of the crosslinking polycationic polymer also affects the pore size and ease of membrane disruption. Generally, higher charge density materials form less porous membranes which are more difficult to disrupt. Optimal reaction conditions suitable for controlling permeability in a given system can readily be determined empirically in view of the foregoing guidelines.

Examples of suitable cross-linking polymers include proteins and polypeptides, either natural or synthetic, having free amino or combinations of amino and imino groups, polyethyleneamines, polyethyleneimines, and polyvinylamines. Polylysine, in both the D and L forms, has been used with success. Proteins such as polyarginine, polycitrulline, or polyornithine are also operable. Polymers in the higher range of positive charge density (e.g., polyvinylamine) vigorously adhere to the anionic groups of the polyanionic molecules and are more difficult to disrupt.

At this point in the encapsulation, capsules may be collected which comprise a "permanent" semipermeable membrane surrounding a gelled solution of gum, cell-type compatible culture medium, and the cells. If the object is simply to preserve the cells in a protective environment, no further steps need be done. However, if mass transfer is to be promoted within the capsules and across the membranes, it is preferred to reliquify the gel to its water-soluble form. This may be done by reestablishing the conditions under which the gum is a liquid, e.g., removing the calcium or other multifunctional cations from the gel. The medium in the capsule can be resolubilized simply by immersing the capsules in phosphate buffered saline, which contains alkali metal ions and hydrogen ions. Monovalent ions exchange with the calcium or other multifunctional ions within the gum when the capsules are immersed in the solution with stirring. Sodium citrate solutions may be used for the same purpose, and serve to sequester the divalent ions. Gum molecules having a molecular weight below the upper limit of permeability of the membrane may subsequently be removed from the intracapsular volume by diffusion.

Lastly, it may be desirable to treat the capsules so as to tie up free amino groups of the like which might otherwise impart to the capsules a tendency to clump. This can be done, for example, by immersing the capsules in a dilute solution of sodium alginate.

From the foregoing it will be apparent that no harsh reagents, extremes of temperature, or other conditions deleterious to the health and viability of the cells need be used in the membrane formation process. Thus, even very sensitive cells such as mammalian hepatocytes, leukocytes, fibroblasts, lymphoblasts, and cells from various endocrine tissues may be encapsulated without difficulty. Of course, cells of microbial origin such as yeasts, molds, and bacteria which are better adapted to survive in hostile environments, as well as inert reagents, solids, or biologically active materials may also be encapsulated without damage.

Encapsulated cells of the type described above may be suspended in maintenance medium or growth medium for storage or culture and will remain free of bacterial infection. If suspended in growth medium, cells which undergo mitosis in vitro will do so within the capsules. Normal in vitro metabolism continues provided the factors needed for metabolic processes are of sufficiently low molecular weight that they can penetrate the capsule membrane, or are encapsulated together with the cells. Metabolic products of the cells (if of a molecular weight below the upper limit of permeability) penetrate the membrane and collect in the medium. The cells in encapsulated form may be stored, shipped, or cultured as desired, and may be released from their protective environment without damage by means of the following process of selectively disrupting the membranes.

DISRUPTION OF MEMBRANE

In accordance with the invention the encapsulated material may be released by a two-step process involving commercially available reagents having properties which do not adversely affect the encapsulated cells.

First, the capsules are separated from their suspending medium, washed with saline and then dispersed, with agitation, in a separate or preferably mixed solution of cations such as calcium ions or other monatomic (low molecular weight, multivalent cation) and a stripping polymer having plural anionic moieties such as polysulfonic acid groups. Polymers containing polyphosphoric or polyacrylic acid moieties may also be used. Heparin, a natural sulfonated polysaccharide, is preferred for disrupting membranes containing cells. The anionic charge of the stripping polymer used must be sufficient to disrupt the salt bridges. Thus the anionic charge density may be equal to or preferably greater than the charge density of the interior polyanionic polymer (e.g., the gum) originally employed to form the membranes. The molecular weight of the stripping polymer should be at least 25,000 daltons or comparable in molecular weight of the polycationic polymer used in forming the membrane. Within the suspension, the calcium ions compete with the polycationic polymer comprising the membrane for anionic sites on the polyanionic polymer. Simultaneously, the stripping polymer dissolved in the solution competes with the polyanionic gum in the membrane for cationic sites on the polycationic polymer. This results in a water-dispersible or prefereably water-soluble complex of, e.g., polylysine and the polyanionic polymer, and in association of the cations with gel molecules.

This step renders the membrane susceptible to subsequent exposure to a sequestering agent which completes the disruption process by taking up di or trivalent ions from the gel. Typically, capsule membrane debris, if any, which remains in the medium can be separated easily from the cells.

The currently preferred solution for the first stage of the selective disruption process comprises 1.1% calcium chloride (w/v) and between 500 to 2,000 units of heparin per milliliter of solution. A volume of microcapsules is added to this solution sufficient to constitute between about 20% and 30% of the total volume of suspension. Calcium chloride and heparin are preferred when disrupting membranes of cell-containing capsules since both reagents are physiologically compatible with most cells and minimize the possibility of cell damage. Mixtures of aluminum salts or other multivalent cations (but not Mg++ ions) may also be used together with the polysulfonic or other acid salt of the type set forth above.

In general, the concentration of the ions and anionic polymer in the solution used in this step may vary widely. Optimum concentrations may be readily determined empirically. The lowest operable concentration for a particular batch of encapsulated cells is preferred.

The currently preferred sequestering agent for performing the selective disruption is sodium citrate, although other alkali metal citrate salts and alkali metal EDTA may also be used. When sodium citrate is employed, the optimum concentration is on the order of 55 mM. Where the capsule membranes being disrupted contain viable tissue, it is preferred that the citrate be dissolved in isotonic saline so as to minimize cell damage.

The invention will be further understood from the following non-limiting examples.

CAPSULE FORMATION

EXAMPLE 1

Encapsulation of Pancreatic Tissue

Islets of Langerhans are obtained from rat pancreas and added to a complete tissue culture (CMRL-1969 Connaught Laboratories, Toronto, Canada) at a concentration of approximately $10^3$ islets per 100 ml. The tissue culture contains all nutrients needed for continued viability of the islets as well as the amino acids employed by the cells for making hormones. One milliliter of an islet suspension containing approximately $3 \times 10^3$ islets is then added to a 2 milliliter volume of 1.2 percent sodium alginate in physiological saline.

Next, a 1.2-1.5 percent calcium chloride solution is used to gel droplets on the order of 500-1000 microns in diameter. After the supernatant solution is removed by aspiration, the gelled droplets are transferred to a breaker containing 15 ml of a solution comprising one part of a 2% 2(cyclohexylamino) ethane sulfonic acid buffer solution in 0.6% NaCl (isotonic, pH=8.2) diluted with 20 parts 1.1% $CaCl_2$. After a 3 minute immersion, the capsules are washed twice in 1% $CaCl_2$.

The capsules are then transferred to a 32 ml solution comprising 1/80 of one percent polylysine (average MW 35,000) in physiological saline. After 3 minutes, the polylysine solution is decanted. The capsules are washed with 1.1% $CaCl_2$, and optionally resuspended for 3 minutes in a solution of polyethyleneimine (MW 40,000-60,000) produced by diluting a stock 3.3% polyethyleneimine solution in morpholino propane sulfonic acid buffer (0.2 M, pH=6) with sufficient 1% $CaCl_2$ to result in a final polymer concentration of 0.12%. The resulting capsules, having "permanent" semipermeable membranes, are then washed twice with 1.1% $CaCl_2$, twice with physiological saline, and mixed with 10 ml of 0.06 percent alginic acid solution.

The capsules resist clumping, and many can be seen to contain islets of Langerhans. Gel on the interior of the capsules is reliquified by immersing the capsules in a mixture of saline and citrate buffer (pH-7.4) for 5 to 10 minutes. Lastly, the capsules are suspended in CMLR 1969 medium.

Under the microscope, these capsules are observed to comprise a thin membrane which encircles an islet within which individual cells can be seen. Molecules having a molecular weight up to about one-hundred thousand can traverse the membranes. This allows oxygen, amino acids, nutrients, and plasma components used in culture media (e.g., lower molecular weight fetal calf serum components) to reach the islet and allows insulin to be excreted.

EXAMPLE 2

Encapsulation of Hepatocytes

The procedure of example 1 is repeated except that 0.5 ml of a liver cell suspension containing about 106 cells per milliliter is used. The ongoing viability of the liver cells has been demonstrated by the dye exclusion technique (trypan blue exclusion) and by labelled leucine incorporation (protein synthesis). It is known that liver tissue, in vitro, can ingest toxins from its environment. Accordingly, toxins of a molecular weight low enough to pass through the semipermeable membranes can be detoxified by the cells.

EXAMPLE 3

Activated Charcoal Encapsulation

The procedure of example 1 is repeated except that particulate activated charcoal is suspended directly in the sodium alginate solution, the milliliter of tissue suspension is omitted, and polylysine of of an average molecular weight of 35,000 is used as a cross-linker. As long as the charcoal particles are smaller than the smallest inside diameter of the capillary used to produce the droplets, charcoal of high surface area surrounded by a semipermeable membrane results. These effectively prohibit the escape of charcoal chips or dust, yet can be used to absorb materials of any pre-selected molecular weight range from fluid passed through the capsules.

EXAMPLE 4

Encapsulation of Human Fibroblasts

Human fibroblasts obtained by treating human foreskin tissue with trypsin and EDTA for 5 minutes at 37° C. in a known manner are suspended in a complete growth medium (CMLR 1969, Connaught Laboratories) supplemented with 40% (v/v) purified fetal calf serum, 0.8% sodium alginate (Sigma) and 200 mg/ml purified calf skin collagen. The density of the cell suspension is about $1.5 \times 10^7$ cells/ml. Temporary alginate capsules are formed as set forth above. Semipermeable membranes are deposited in surface layers of the capsules by suspending them in a 0.005% (w/v) aqueous solution of poly L lysine, (MW 40,000 daltons) for 3 minutes.

The resulting capsules are suspended in CMLR-1969 supplemented with 10% fetal calf serum. The foregoing steps are all conducted at 37° C. After incubation at the same temperature, the capsules, if examined under the microscope, will be found to contain fibroblasts which have undergone mitosis and display three-dimensional fibroblastic morphology within the microcapsules.

SELECTIVE DISRUPTION OF THE MEMBRANES

EXAMPLE 5

Microcapsules from any of examples 1–4 may be treated as follows in order to selectively disrupt the capsule membranes without damage to the encapsulated core material.

Microcapsule suspensions are allowed to settle and the suspension medium is aspirated off. The capsules are washed twice with saline. The washed capsules are then mixed with 3 to 4 volume of saline containing heparin in various concentrations as set forth below and 1.1% (w/v) $CaCl_2$. Capsules having alginate enclosed therewithin, on completion of this step, display a gelled, shape-retaining interior core. The suspension is agitated at 37° C. for 10 minutes, after which the capsules are allowed to settle, the supernatant is aspirated off, and the capsules are washed twice with 3.0 ml of 0.15 M NaCl. After aspiration of the second wash solution, the capsules are mixed with 2.0 ml of a mixed solution comprising equal volumes of 110 mM sodium citrate and 0.15 M NaCl (pH=7.4).

Capsule membranes which had been treated with 1,000 units/ml heparin and vortexed in the NaCl-NaCitrate solution for 1 minute were completely disintegrated. The same result is achieved with capsules treated with 2,000 units/ml heparin for 2 minutes, followed by 15–30 seconds of hand vortexing. Lower concentrations of heparin are preferred as the possibility of cell damage is decreased.

After dissolution of the membranes any membrane debris may be removed by aspiration and washing. After the released cells are resuspended in culture medium, they may be tested by the tryptan blue dye exclusion technique and will be found to be in a healthy, viable condition, with relatively few cells exhibiting dye uptake.

EXAMPLE 6

Capsules produced in accordance with example 3 are treated, after washing, with a 3–4 volume solution containing 1,000 units/ml heparin and 1.0% $AlCl_3$ for 6 minutes with agitation. After aspiration of the supernatant, the core material is released by vortexing the capsules with a 0.1 M solution of sodium citrate for 30–90 seconds.

EXAMPLE 7

The procedure of example 6 is repeated except that 0.10 M EDTA (sodium form) at a pH of 7.0 is used in place of the sodium citrate, resulting in rapid disruption of the capsule membranes.

EXAMPLE 8

Capsules produced in accordance with example 3 are treated, after washing, with a 3–4 volume solution containing 10 mg/ml of polyvinyl sulfate (mw approximately 50,000 daltons) and 1% $CaCl_2$. Post treatment with 0.10 M sodium citrate results in essentially complete dissolution of the capsules.

Other embodiments are within the following claims.

What is claimed is:

1. A method of encapsulating a core material within a protective environment and of subsequently releasing said core material, said method comprising:
   encapsulating said core material by the steps of:
   A. placing the core material in an aqueous medium which contains a water-soluble polymer containing anionic groups and having a first charge density;
   B. forming the medium into droplets;
   C. subjecting the droplets to a solution of multivalent cations to gel the droplets as discrete, shape-retaining, water-insoluble temporary capsules;
   D. cross-linking surface layers of said temporary capsules to produce semipermeable membranes about said droplets by subjecting them to a first polymer containing cationic moieties reactive with the anionic groups of said water-soluble polymer;
   and releasing said core material by the steps of:
   E. exposing the capsules resulting from step D to a solution of monatomic, multivalent cations and a stripping polymer having plural anionic moieties, said stripping polymer having a charge density at least equal to said first charge density;
   F. allowing said monatomic cations to compete with said first polymer for anionic groups on the water-soluble polymer and allowing said stripping polymer having plural anionic moieties to compete with said water-soluble polymer for cationic sites on said first polymer; and
   G. sequestering monatomic cations associated with said water-soluble polymer after step F.

2. The method of claim 1 wherein the water-soluble polymer is a polysaccharide.

3. The method of claim 1 including the additional step of removing the multivalent ions contained within said capsules to resolubilize the gelled interior of the membranes of said capsules after step D and prior to step E.

4. The method of claim 1 wherein said core material comprises cells and said aqueous medium is physiologically compatible with said cells.

5. The method of claim 1 wherein said first polymer is selected from the group consisting of:

(a) proteins comprising plural amino acid units having free amino groups;
(b) proteins comprising plural amino acid units having free imino groups;
(c) polypeptides comprising plural amino acid units having free amino groups;
(d) polypeptides comprising plural amino acid units having free imino groups;
(e) polyvinyl amines;
(f) polyethyleneimines;
(g) polyethyleneamines; and
(h) mixtures thereof.

6. The method of claim 1 wherein said first polymer comprises multiple moieties selected from the group consisting of imino and amino groups.

7. The method of claim 4 wherein said cells comprise mammalian cells.

8. The method of claim 1 wherein said core material comprises cells, said method comprising the additional step, between steps D and E, of suspending the capsules resulting from step D in a medium sufficient to maintain said cells in vitro.

9. The method of claim 1 wherein said sequestering step G is effected by exposing said capsules, after step F, to a solution containing a chelate.

10. The method of claim 9 wherein said chelate is selected from the group consisting of citrate ions and EDTA ions.

11. The method of claim 1 wherein said first polymer comprises a polypeptide, said water-soluble polymer comprises alginate, and said stripping polymer having plural anionic moieties is heparin.

12. The method of claim 1 wherein said water-soluble polymer comprises alginate.

13. The method of claim 1 wherein said stripping polymer comprises heparin and said cation comprise $Ca^{++}$.

14. The method of claim 1 wherein said stripping polymer is selected from the group consisting of:
(a) polysulfonic acids;
(b) polyphosphoric acids;
(c) salts thereof; and
(d) mixtures thereof.

15. The method of claim 1 wherein said stripping polymer is a polysulfonic acid salt polymer.

16. The method of claim 1 wherein said stripping polymer has a charge density greater than said first charge density.

17. The method of claim 4 wherein said first polymer comprises a polypeptide, said water-soluble polymer comprises alginate, said cations comprise calcium, and said stripping polymer comprises heparin.

18. The method of claim 17 wherein said sequestering step is effected with citrate dissolved in a solution physiologically compatible with said cell.

* * * * *